United States Patent [19]

Louderback

[11] 4,158,544
[45] Jun. 19, 1979

[54] PROCESS FOR PREPARING A BIOLOGICAL COMPOSITION FOR USE AS A REFERENCE CONTROL IN DIAGNOSTIC ANALYSIS

[75] Inventor: Allan L. Louderback, Temple City, Calif.

[73] Assignee: Beckman Instruments, Inc., Fullerton, Calif.

[21] Appl. No.: 925,483

[22] Filed: Jul. 17, 1978

[51] Int. Cl.$^2$ .............................................. G01N 33/16
[52] U.S. Cl. .................................... 23/230 B; 252/408
[58] Field of Search .......................... 23/230 B, 230 R; 252/408; 424/101

[56] References Cited

U.S. PATENT DOCUMENTS

| | | | |
|---|---|---|---|
| 2,664,403 | 12/1953 | Weichselbaum | 252/408 |
| 2,770,602 | 11/1956 | Weichselbaum | 252/408 |
| 3,466,249 | 9/1969 | Anderson | 252/408 |
| 3,629,142 | 12/1971 | Marbach | 23/230 B |
| 3,876,375 | 4/1975 | Maurukas | 23/230 B |

*Primary Examiner*—R. E. Serwin

*Attorney, Agent, or Firm*—Robert J. Steinmeyer; Robert S. Frieman

[57] ABSTRACT

A process for making a biological composition for use as a blood serum reference composition in diagnostic analysis. The process comprises:
(a) adding calcium to citrated plasma and mixing well to form decitrated plasma;
(b) adding thrombin to the decitrated plasma and mixing well to form a clot of fibrin;
(c) performing at least one freeze-thaw routine on the clot to cause the fibrin to contract;
(d) removing the fibrin to thereby obtain serum;
(e) molecular washing and ultrafiltering the serum and thereby obtaining concentrated serum; and
(f) adding to the concentrated serum at least one alkylene polyol having from 2-5 carbon atoms in an amount such that said composition's non-biological component comprises from about 40 to about 85 weight percent water and from about 15 to about 60 weight percent of said alkylene polyol.

10 Claims, No Drawings

PROCESS FOR PREPARING A BIOLOGICAL COMPOSITION FOR USE AS A REFERENCE CONTROL IN DIAGNOSTIC ANALYSIS

BACKGROUND OF THE INVENTION

1. Field of the Invention

This invention relates to a method of preparing a laboratory standard material and, more particularly, to a method of preparing blood serum reference compositions of the type described in U.S. Pat. No. 3,876,375 (hereinafter referred to as the Maurukas patent), the Maurukas patent being incorporated herein by this reference.

2. Description of the Prior Art

The Maurukas patent discloses a biological composition for use as a reference control in diagnostic analysis. The Maurukas composition comprises, in its nonbiological component, from about 60 to about 80 weight percent water, from about 20 to about 40 weight percent of at least one alkylene polyol having from 2 to 5 carbon atoms, the remainder being chiefly at least one natural biological material selected from a group consisting of blood serum, enzymes, metabolites, electrolytes, and hormones. However, the method disclosed in the Maurukas patent for producing such a biological composition is commercially impractical. For example, Maurukas employed human blood serum obtained from a clinical laboratory. This source of human blood serum is impractical for use on a commercial scale. The method described in the Maurukas patent begins with human blood serum obtained from clinical laboratories. While such sources may be tapped for small quantities of human blood serum, there are far too few such sources to provide the large quantities of human blood needed in the commercial manufacture of reference controls. In fact, citrated plasma, rather than human blood serum is the only viable source for obtaining enough human blood necessary for commercial production. Citrated plasma comes from plasma pheresis blood donor banks which specialize in selling citrated plasma. Citrated plasma is obtained from donors via plasma pheresis at a rate of one liter per week per donor and also has the additional advantage over clinical laboratory pooled human blood in that it is checked for hepatitis and venereal disease. Further, the method disclosed by the Maurukas patent for processing human blood serum entails the loss of substantial quantities of protein. The Maurukas process entails freezing a block of pool blood serum and then slowly thawing the frozen block at a controlled temperature over a 3 to 7 day period to obtain a desired volume of concentrated protein. Over 25% of the protein is left behind in the frozen matrix discarded via Maurukas' above process.

SUMMARY OF THE INVENTION

This invention encompasses a commercially viable method of preparing a biological composition of the type disclosed by Maurukas wherein the source of the raw material is citrated plasma and wherein less than 0.10% protein is lost in the manufacturing process.

The method encompassed by the instant invention comprises (a) adding calcium to citrated plasma and mixing well to form decitrated plasma;

(b) adding thrombin to the decitrated plasma and mixing well to form a clot of fibrin;

(c) performing at least one freeze-thaw routine on the clot to cause the fibrin to contract;

(d) removing the fibrin to thereby obtain serum;

(e) molecular washing and ultrafiltering the serum and thereby obtaining concentrated serum; and (f) adding to the concentrated serum at least one alkylene polyol having from 2 to 5 carbon atoms in an amount such that such composition's non-biological component comprises from about 40 to about 85 weight percent water and from about 15 to about 60 weight percent of alkylene polyol.

DESCRIPTION OF THE PREFERRED EMBODIMENTS

The process of the instant invention comprises:

(a) adding calcium to citrated plasma and mixing well to form decitrated plasma;

(b) adding thrombin to the decitrated plasma and mixing well to form a clot of fibrin;

(c) performing at least one, preferably at least three, and more preferably three or four, freeze-thaw routines on the clot to cause the fibrin to contract;

(d) removing the fibrin to thereby obtain serum;

(e) molecular washing and ultrafiltering the serum to thereby obtain concentrated serum; and (f) adding to the concentrated serum at least one alkylene polyol having from 2 to 5 carbon atoms in an amount such that the composition's non-biological component comprises from about 40 to about 85, preferably from about 60 to about 80, weight percent water and from about 15 to about 60, preferably from about 20 to about 40, weight percent of the alkylene polyol.

Enough calcium salt is added to the citrated plasma to overcome the citrate present in the plasma. Typically, at least 10 milligrams of calcium salt per 100 milliliter of plasma is added. Preferably, at least 20 milligrams of calcium salt is added per 100 milliliters of plasma. It is also preferred that no more than about 40 milligrams of calcium be added per 100 milliliter of plasma. If too mcuh calcium salt is added, the concentration of calcium in the final product will be too high for diagnostic use.

The thrombin added to the decitrated plasma can be of any animal source such as bovine or equine. Preferably, at least 1, and more particularly at least 3, NIH units per ml serum of thrombin is added. Because of the waste entailed thereby, it is undesirable to add more than 10 NIH units/ml serum of thrombin to the plasma.

After adding the thrombin, one should let the plasma sit for an amount of time sufficient for a firm clot to form in the plasma, e.g., from about 5 minutes to about 6 hours at room temperature.

The freeze-thaw routine can be conducted by any conventional method known to those skilled in the art. For example, the freezing can be performed at from about $-5°$ to about $-20°$ C. Although time is not critical, it is preferred to conduct the freezing process for at least 8 hours. The frozen material can be allowed to thaw via any convenient procedure. For example, the thawing can take place at about $15°$ to about $35°$ C. in a water bath. The thawing preferably is conducted for that period of time which is necessary to completely liquefy the solid mass. This time usually entails from about 2 to about 5 hours.

It should be noted that there is a fundamental functional difference between the freeze-thaw process employed in the instant invention and the freeze-thaw process as described in the Maurukas patent. In the Maurukas patent, the purpose of the freeze-thaw process is to remove a volume of water from the serum and thereby concentrate the protein. As discussed above, about 25% or more protein is lost in the frozen matrix discarded by Maurukas.

In contrast, the instant invention employs a freeze-thaw process to contract the fibrin clot in transforming the plasma into serum. The contracted fibrin is removed from the serum and discarded. Less than 0.10% protein is lost in the discarded fibrin clot.

The fibrin can be removed from the material by any procedure well known to those skilled in the art. For example, the material can be either poured into a filter system such as a collander or centrifuged in order to remove the fibrin therefrom.

A molecular wash can be performed by any method well known to those skilled in the art. Typically, distilled or deionized water is added to the serum.

The ultrafiltration steps can also be performed by any method well known to those skilled in the art. The ultrafilter preferably has a nominal molecular weight (m.w.) discrimination of about 10,000. By employing an untrafilter with a molecular weight discrimination of about 10,000, one is able to obtain fast flow of serum through the ultrafilter, while removing low molecular items (e.g., glucose, 180 m.w.; salt, 58 m.w.; calcium, 40 m.w.; water, 18 m.w.). Nevertheless, proteins are not removed from the serum because they have a molecular weight greater than 50,000 (e.g., albumin has a molecular weight of about 64,000).

If one desires to inactivate all endogenous enzyme action, one can acid treat the serum after step (d) by first dropping the pH thereof to from about 3.0 to about 4.5, preferably about 4, and then raising the pH of the serum to from about 6.0 to about 9.0, preferably from about 6.5 to about 8.5. The pH of the serum can be lowered by any suitable acid, e.g., HCl, and can be raised by any suitable base, e.g., NaOH.

In addition, it is also preferred to contact the concentrated serum after step (e) or contact the reconcentrated serum after step (f) with fumed silicon dioxide, mix, and separate the fumed silicon dioxide therefrom. The latter procedure imparts a better aesthetic appearance to the serum and also removes any lipids and triglycerides therefrom.

The following example is provided for the purpose of further illustration only and are not intended to be limitations upon the disclosed invention.

EXAMPLE 1

Serum having an initial concentration of 5.6 gm/dl protein was passed through a Millipore Pellicon ® Cassette System ultrafiltration unit. The ultrafiltration unit has two effluent parts, one of which is the retentate and the other is the filtrate. The filtrate contained the water and low molecular compounds removed from the serum and was later discarded. The retentate port contained the concentrated serum which, after being recycled, had a protein concentration of 14–16 mg/dl of total protein.

The filtrate before being discarded was checked for protein by Exton's method and found to be negative, i.e., devoid of any protein.

The above example clearly shows that no protein is lost during the ultrafiltration process. Therefore, the only protein lost in the method of the instant invention is that present in the fibrin clot. As pointed out above, this amounts to a protein loss of less than 0.10%.

Based on this disclosure, many other modifications and ramifications will naturally suggest themselves to those skilled in the art. These are intended to be comprehended as within the scope of the invention as claimed herein.

The embodiments of the invention in which an exclusive property or privilege is claimed are defined as follows:

1. A process for making a biological composition for use as a blood serum reference composition in diagnostic analysis comprising:
   (a) adding calcium to citrated plasma and mixing well to form decitrated plasma;
   (b) adding thrombin to said decitrated plasma and mixing well to form a clot of fibrin;
   (c) performing at least one freeze-thaw routine on said clot to cause the fibrin to contract;
   (d) removing the fibrin to thereby obtain serum;
   (e) molecular washing and ultrafiltering the serum and thereby obtaining concentrated serum; and
   (f) adding to the concentrated serum at least one alkylene polyol having from 2–5 carbon atoms in an amount such that said composition's non-biological component comprises from about 60 to about 80 weight percent water and from about 20 to about 40 weight percent of said alkylene polyol.

2. The process of claim 1 wherein after step (d), the serum is acid-treated by first dropping the pH thereof to from about 3.0 to 4.5 to thereby inactivate all endogenous enzyme action and then raising the pH of said serum to from about 6.0 to about 9.0.

3. The process of claim 2 wherein said pH is first dropped to about 4 and then raised to from about 6.5 to about 8.5.

4. The process of claim 2 wherein at least three freeze-thaw routines are performed on said clot.

5. The process of claim 4 wherein four freeze-thaw routines are performed on said clot.

6. The process of claim 2 wherein after step (e), fumed silicon dioxide is contacted with said concentrated serum, mixed, and separated therefrom.

7. The process of claim 2 wherein after step (f), fumed silicon dioxide is contacted with said alkylene polyol containing biological composition, mixed, and separated therefrom.

8. The process of claim 1 wherein after step (e), fumed silicon dioxide is contacted with said concentrated serum, mixed, and separated therefrom.

9. The process of claim 1 wherein after step (f), fumed silicon dioxide is contacted with said alkylene polyol containing biological composition, mixed, and separated therefrom.

10. The process of claim 1 wherein at least three freeze-thaw routines are performed on said clot.

* * * * *